United States Patent [19]

Dolak et al.

[11]  4,306,021
[45]  Dec. 15, 1981

[54] COMPOSITION OF MATTER AND PROCESS

[75] Inventors: Lester A. Dolak, Plainwell; LeRoy E. Johnson, Kalamazoo, both of Mich.

[73] Assignee: The Upjohn Company, Kalamazoo, Mich.

[21] Appl. No.: 139,099

[22] Filed: Apr. 10, 1980

[51] Int. Cl.$^3$ .................... C12N 1/20; C12P 13/00; C12P 1/06
[52] U.S. Cl. ................................ 435/128; 435/169; 435/253; 435/886; 424/116; 424/121
[58] Field of Search ............... 435/169, 886, 128, 253; 424/116, 121

[56]  References Cited
PUBLICATIONS

Kimura et al., *The Journal of Antibiotics*, vol. XXIII, No. 9, 461–463 (1970).

*Primary Examiner*—Esther M. Kepplinger
*Attorney, Agent, or Firm*—Roman Saliwanchik

[57]  ABSTRACT

Novel antibiotic U-60, 394 producible in a fermentation under controlled conditions using a biologically pure culture of the microorganism *Streptomyces woolenses*, Dietz and Li sp.n., NRRL 12113. This antibiotic is strongly active against various Gram-positive bacteria, for example, *Staphylococcus aureus* and *Streptococcus hemolyticus*. It is also strongly active against the Gram-negative bacterium *Streptococcus pneumoniae*. Thus, antibiotic U-60, 394 can be used in various environments to eradicate or control such bacteria.

8 Claims, 4 Drawing Figures

COMPOSITION OF MATTER AND PROCESS

BACKGROUND OF THE INVENTION

Antibiotic U-60,394 has similarities to matchamycin, a known antibiotic. See A. Kimura and H. Nishimura, J. Antibiotics 33, 461 (1970). Matchamycin has the molecular formula $C_{20}H_{13}O_6N_3Cu$ and is produced by S. amagasakensis. It can be differentiated from U-60,394 by melting point, UV spectrum, IR spectrum, and mass spectrum. S. amagasakensis grown in U-60,394 medium does not produce U-60,394, nor does S. woolensis when grown in the Japanese medium produce matchamycin.

BRIEF SUMMARY OF THE INVENTION

Antibiotic U-60,394 is producible in a fermentation under controlled conditions using a biologically pure culture of the new microorganism Streptomyces woolensis, Dietz and Li sp.n., NRRL 12113.

Antibiotic U-60,394 is strongly active against various Gram-positive bacteria. Further, the base addition salts of antibiotic U-60,394 are also active against these bacteria. Thus, antibiotic U-60,394 and its salts can be used to disinfect washed and stacked food utensils contaminated with S. aureus. They can also be used as disinfectants on various dental and medical equipment contaminated with S. aureus. Still further, antibiotic U-60,394 and its salts can be used as a bacteriostatic rinse for laundered clothes, and for impregnating papers and fabrics; and, they are also useful for suppressing the growth of sensitive organisms in plate assays and other microbiological media.

DETAILED DESCRIPTION OF THE INVENTION

Chemical and Physical Properties of Antibiotic U-60,394:

Molecular Weight: 391.08014 (high resolution spectrometry)

Molecular Formula: $C_{20}H_{13}N_3O_6$

Color and Form of Crystals: Yellowish-green needles.

Figure 3:
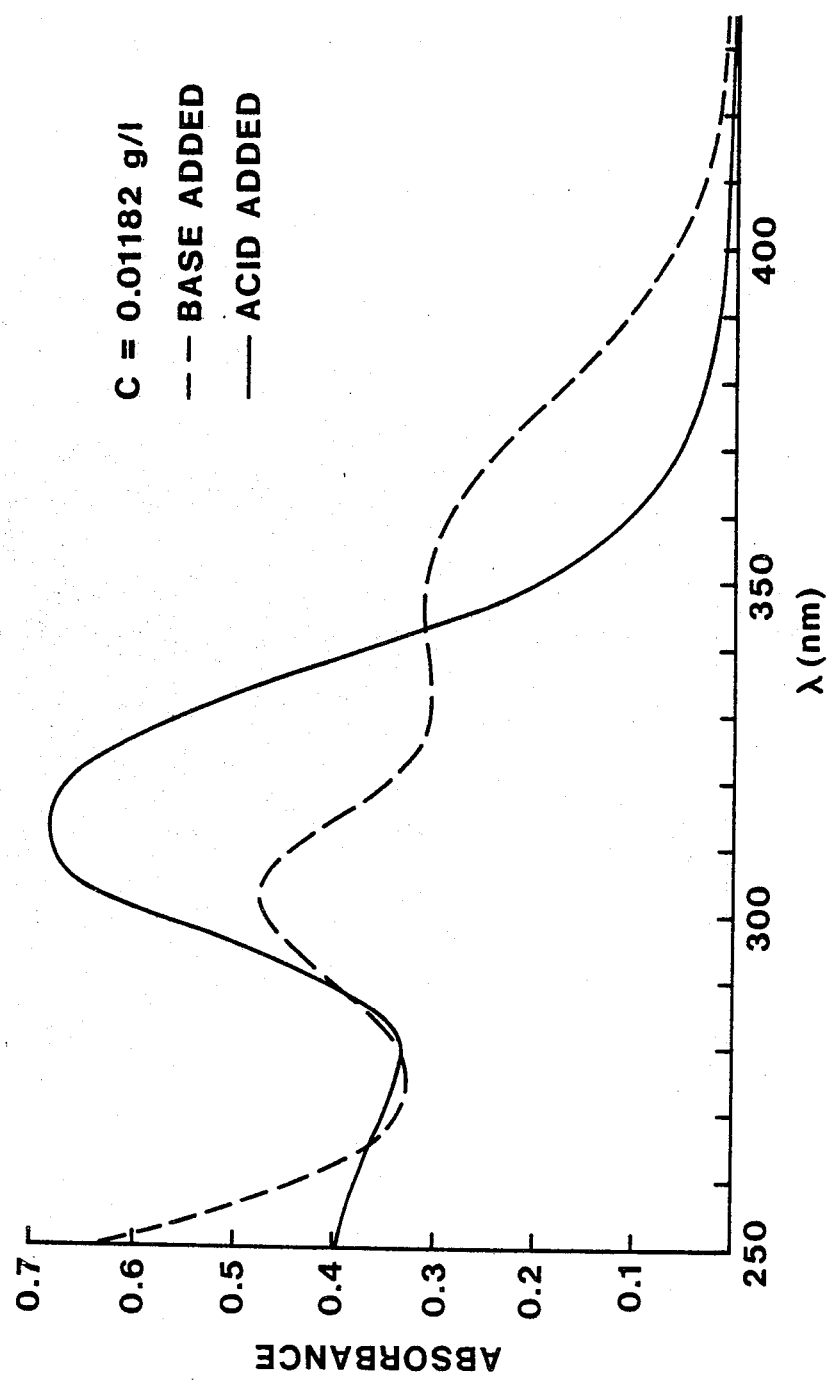

Ultraviolet Absorption Spectrum:

The UV spectrum of antibiotic U-60,394 is shown in FIG. 3 of the drawings. The solution of antibiotic U-60,394 in methanol displayed absorption as follows:

| Solvent | λ max | Absorptivity (ε) |
| --- | --- | --- |
| Methanol | 310 nm | 22,275 |
| 0.01N $H_2SO_4$ in MeOH | 311 | 22,857 |
| 0.01N KOH in MeOH | 303; 347 | 15,796; 10,389 |

Melting Point: 265° C. to 266° C. with decomposition.

Figure 4:
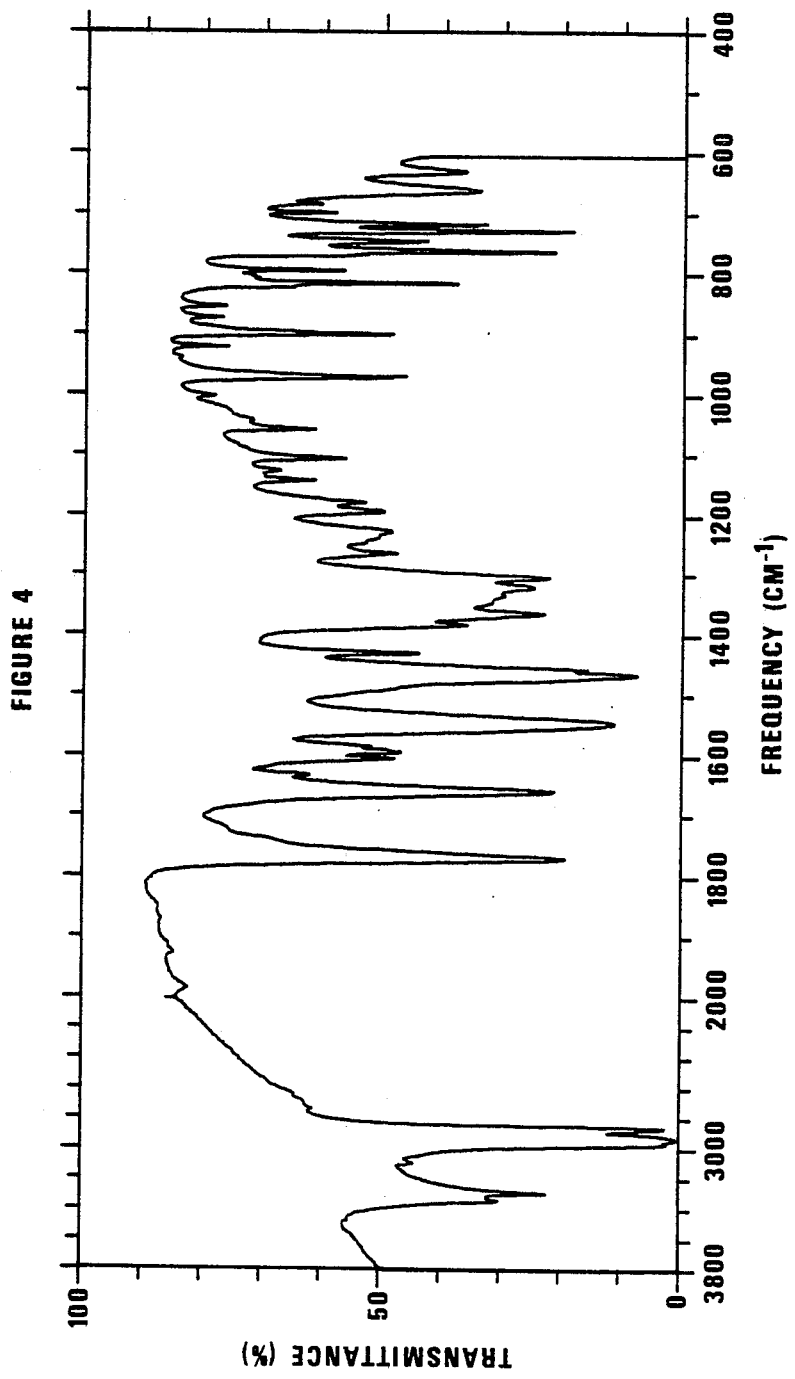

Infrared Absorption Spectrum:

Antibiotic U-60,394 has a characteristic infrared absorption spectrum in a mineral oil mull as shown in FIG. 4 of the drawings. Peaks are observed at the following wave lengths.

| Band Frequency[1] | Intensity[2] | Band Frequency[1] | Intensity[2] |
| --- | --- | --- | --- |
| 3342 | 30 | 1298 | 22 |
| 3289 | 22 | 1256 | 47 |
| 3098 | 45 | 1237 | 52 |
| 3086 | 44 | 1229 | 50 |
| 2955 | 2 | 1220 | 48 |
| 2924 | 1 | 1186 | 49 |
| 2869 | 7,sh | 1172 | 53 |
| 2854 | 2 | 1136 | 61 |
| 2728 | 62 | 1121 | 67 |
| 2630 | 65 | 1100 | 56 |
| 1978 | 83 | 1052 | 61 |
| 1918 | 85 | 1038 | 71 |
| 1868 | 87 | 1022 | 76,sh |
| 1848 | 88 | 996 | 78 |
| 1764 | 19 | 964 | 46 |
| 1714 | 76,sh | 932 | 84 |
| 1652 | 21 | 914 | 76 |
| 1625 | 62 | 893 | 48 |
| 1598 | 47 | 867 | 77 |
| 1587 | 46 | 849 | 76 |
| 1579 | 51 | 810 | 38 |
| 1540 | 11 | 802 | 70 |
| 1458 | 7 | 789 | 57 |
| 1451 | 15 | 763 | 53 |
| 1424 | 43 | 757 | 22 |
| 1377 | 35 | 740 | 42 |
| 1359 | 23 | 722 | 18 |
| 1339 | 32 | 712 | 32 |
| 1328 | 29 | 692 | 59 |
| 1315 | 24 | 678 | 60 |
|  |  | 656 | 33 |
|  |  | 625 | 36 |

[1]Wavenumbers (cm$^{-1}$)
[2]Percent transmittance (% T), sh. = shoulder Intensity at 3800 cm$^1$ is 59% T. Minimum intensity at 1804 cm$^{-1}$ is 89.6% T.

Figure 1:
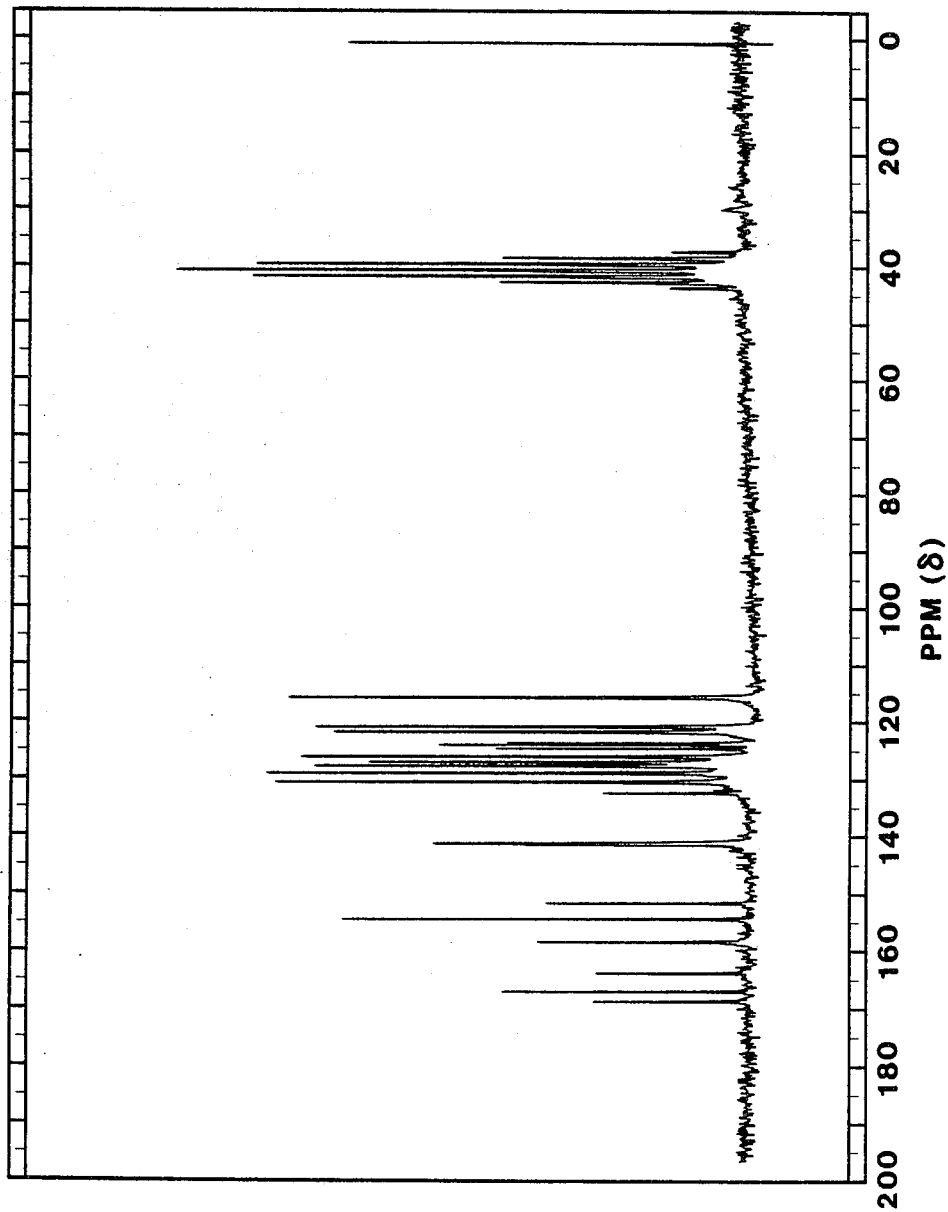

$^{13}$C-Nuclear Magnetic Resonance (NMR) Spectrum:

The $^{13}$C-NMR spectrum of antibiotic U-60,394 is shown in FIG. 1 of the drawings. The $^{13}$C-NMR spectrum was observed on a Varian CFT-20 Spectrometer on a solution (ca. 0.5 ml., ca. 200 mg./ml.) of the sample of the antibiotic in deutero-dimethylsulfoxide (d$_6$-DMSO). The spectrum was calibrated against internal tetramethylsilane and frequencies were recorded in ppm downfield from tetramethylsilane.

Figure 2:
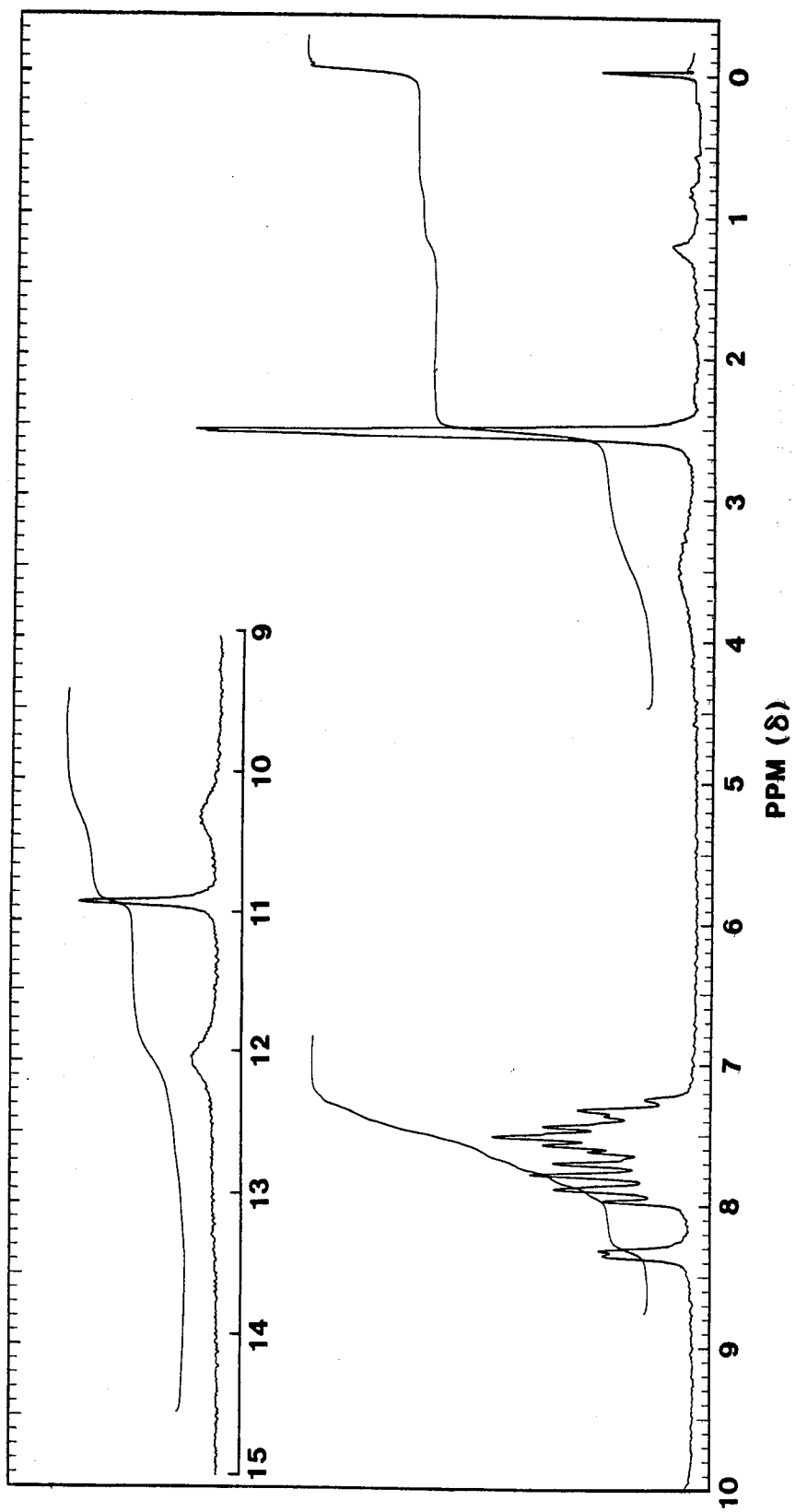

Proton Magnetic Resonance ($^1$H-NMR) Spectrum:

The $^1$-H-NMR spectrum of antibiotic U-60,394 at 100 MHZ is shown in FIG. 2 of the drawings. The $^1$H-NMR spectrum was observed on a Varian XL-100-15 Spectrometer on a solution (ca. 0.5 ml., ca. 150 mg./ml.) of the sample of the antibiotic in deutero-dimethylsulfoxide (d$_6$-DMSO). The spectrum was calibrated against internal tetramethylsilane and frequencies were recorded in ppm downfield from tetramethylsilane.

Solubilities:

Antibiotic U-60,394 is soluble in methanol and acetone with difficulty, and easily soluble in ethyl acetate, methylene chloride, and dimethylsulfoxide. It is insoluble in water.

Antimicrobial Spectrum of Antibiotic U-60,394:

Antibiotic U-60,394 is active against various Gram-positive bacteria and S. pneumoniae as shown in the following tables.

Assay:

The antibacterial assay is a standard microplate broth dilution assay. The MIC is determined by standard methods using two-fold dilutions of the antibiotic in Brain Heart Infusion Broth (Difco Lab., Detroit, Mi). The inocula are overnight cultures of the test organisms, diluted so that the final population contains approximately 10$^5$ cells/ml. The solutions are incubated at 28° to 37° C. for 24 hours. The lowest antibiotic concentration which allows no growth=MIC or minimum inhibitory concentration.

| Microorganism | | Minimum Inhibitory Concentration (mcg/ml) |
|---|---|---|
| Staphylococcus aureus | 284 UC 76 | 7.8 |
| Staphylococcus aureus | UC 570 | 2.0 |
| Staphylococcus aureus | UC 746 | 7.8 |
| Streptococcus hemolyticus | UC 152 | ≦0.5 |
| Streptococcus faecalis | UC 694 | 500 |
| Escherichia coli | UC 45 | >1000 |
| Proteus vulgaris | UC 93 | >1000 |
| Klebsiella pneumoniae | UC 58 | >1000 |
| Salmonella schottmuelleri | UC 126 | >1000 |
| Pseudomonas aeruginosa | UC 95 | >1000 |
| Streptococcus pneumoniae | UC 41 | 1.0 |

"UC" is a registered trademark of The Upjohn Company Culture Collection. These cultures can be obtained from The Upjohn Company in Kalamazoo, Mi., upon request.

THE MICROORGANISM

The microorganism used for the production of antibiotic U-60,394 is a biologically pure culture of *Streptomyces woolensis*, Dietz and Li sp.n., NRRL 12113.

A subculture of this microorganism can be obtained from the permanent collection of the Northern Regional Research Laboratory, U.S. Department of Agriculture, Peoria, Il., U.S.A. Its accession number in this depository is NRRL 12113. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

*S. woolensis* was found to produce an antibiotic very similar to matchamycin. *S. woolensis* was found to be very similar on Ektachrome (Table 1) to the matchamycin producer *Streptomyces amagasakensis* E-753 (Kimura, A., and H. Nishimura. 1970. Matchamycin: A new antibiotic produced by Streptomyces E-753, J. Antibiotics 23:461-463). Both cultures are melanin negative. They are both members of the genus Streptomyces as determined by the detection of L-diaminopimelic acid in whole cell hydrolysates, the presence of vegetative hyphae producing a well-developed mycelium, and the production of aerial mycelium which sporulates to form a mass of color. The sporulating mycelial mass of the two cultures is superficially similar. The spores of the new culture are in long flexuous to open spiral chains; the spores of *S. amagasakensis* are in open to tight spiral chains. This may be observed by light and scanning electron microscopy. The surface detail of the spores of the two cultures, as observed by scanning electron microscopy, is distinctly different. The new culture has spores with a type of surface appendage not reported in the literature for members of the genus Streptomyces. The spore surface is covered with wooly-like protrusions which overlap to give a matted appearance. The spore surface of *S. amagasakensis* is smooth with a slight ridging to spiny. The spines are abundant and short. The spores of both cultures are spherical to elliptical. The cultures are further differentiated by their reference color characteristics (Table 2) and their growth on carbon compounds in the synthetic medium of Shirling and Gottlieb (Table 3). There are no significant differences in their cultural and biochemical characteristics (Table 4).

The cultures in their color pattern on Ektachrome could be considered related. However, the distinctly different microscopic characteristics and the subtle differences in growth on carbon compounds and in reference color characteristics warrant the designation of a new species of Streptomyces. The name *Streptomyces woolensis* is proposed based on the distinctive wooly appearance of the spores of the new culture. It is proposed that this type species be designated the type subspecies should cultures with similar properties be found. This is in accordance with the Rules of Nomenclature in the International Code of Nomenclature of Bacteria (Lapage, S. P., P. H. A. Sneath, E. F. Lessel, V. B. D. Skerman, H. P. R. Seeliger, and W. A. Clark, eds. 1975. International Code of Nomenclature of Bacteria, 1976 Revision. American Society for Microbiology, Washington, D.C.).

*Streptomyces woolensis* Dietz and Li sp.nov. NRRL 12113.

Color Characteristics:

The aerial mycelium is reddish to brownish gray on Ektachrome (Table 1) and gray (Gy) when compared with the chips in the Tresner and Backus (Tresner, H. D., and E. J. Backus. 1963. System of color wheels for streptomycete taxonomy. Appl. Microbiol. 11:335-338) color wheels. Reference color characteristics are given in Table 2. The culture is melanin negative.

Microscopic Characteristics:

Spores are borne in long, flexuous to open spiral chains. The spores, when observed by the scanning electron microscope, are found to be covered with wooly appendages. The wooly appendages look like intertwined fibers. (This surface detail has not been reported in the literature.)

Growth on Carbon Compounds:

See Table 3.

Whole Cell Analysis:

L-diaminopimelic acid was detected.

Cultural and Biochemical Characteristics:

See Table 4.

Temperature:

Growth was good at 24° C.-32° C., moderate at 18° C. and 37° C. There was no to trace growth at 45° C. and no growth at 55° C.

The methods used herein are those cited in Becker et al. (Becker, B., M. P. Lechevalier, and H. A. Lechevalier. 1966. Chemical composition of cell wall preparations from strains of various form-genera of aerobic actinomycetes. Appl. Microbiol. 13:236-243), Dietz (Dietz, A. 1954. Ektachrome transparencies as aids in actinomycete classification. Ann. N. Y. Acad. Sci. 60: 152-154) (Dietz, A. 1967. *Streptomyces steffisburgensis* sp. n. J. Bacteriol. 94:2022-2026), Dietz and Mathews (Dietz, A., and J. Mathews. 1971. Classification of Streptomyces spore surfaces into five groups. Appl. Microbiol. 21:527-533), and Shirling and Gottlieb (Shirling, E. B., and D. Gottlieb. 1966. Methods for characterization of Streptomyces species. Int. J. Syst. Bacteriol. 16:313-340).

TABLE 1

Color Characteristics* of *Streptomyces woolensis* and *Streptomyces amagasakensis* on Ektachrome**

| Agar Medium | Determination | S. woolensis NRRL 12113 Chip | Color | S. amagasakensis ATCC 21325 Chip | Color |
|---|---|---|---|---|---|
| Bennett's | S | 63 | light brownish gray | 23 | dark reddish gray |
|  | R | 77 | moderate yellowish brown | 77 | moderate yellowish brown |
| Czapek's sucrose | S | 63 | light brownish gray | 266 | dark gray |
|  | R | 77 | moderate yelowish brown | 63 | light brownish gray |
| Maltose-tryptone | S | 63 | light brownish gray | 23 | dark reddish gray |
|  | R | 77 | moderate yellowish brown | 55 | strong brown |
| Peptone-iron | S | 70 | light orange yellow | 70 | light orange yellow |
|  | R | 68 | strong orange yellow | 68 | strong orange yellow |
| 0.1% tyrosine | S | 22 | reddish gray | 22 | reddish gray |
|  | R | 38 | dark reddish orange | 38 | dark reddish orange |
| Casein starch | S | 23 | dark reddish gray | 23 | dark reddish gray |
|  | R | 63 | light brownish gray | 63 | light brownish gray |

*Color was determined by comparison with NBS Color Chips (SP 440. Color: Universal Language and Dictionary of Names. U.S. Government Printing Office, Washington, D.C. 20402) (SRM 2106. ISCC-NBS Centroid Color Charts. Office of Standard Reference Material, Room B311, Chem. Building. National Bureau of Standards, Washington, D.C. 20234).
S = Surface
R = Reverse
Color determinations made on tubes incubated 7 days at 28° C.
**(Dietz, A. 1954. Ektachrome transparencies as aids in actinomycete classification. Ann. N.Y. Acad. Sci. 60:152–154.

TABLE 2

Reference Color Characteristics* of *S. woolensis* and *S. amagasakensis*

| Agar Medium | Determination | S. woolensis NRRL 12113 Chip | Color | S. amagasakensis ATCC 21325 Chip | Color |
|---|---|---|---|---|---|
| Bennett's | S | 89 | pale yellow | 22 | reddish gray |
|  | R | 89 | pale yellow | 72 | dark orange yellow |
|  | P | — | — | — |  |
| Czapek's sucrose | S | 10 | pinkish gray | 23 | dark reddish gray |
|  | R | 86 | light yellow | 90 | grayish yellow |
|  | P | 89 | pale yellow | — | — |
| Maltose tryptone | S | 22 | reddish gray | 63 | light brownish gray |
|  | R | 78 | dark yellowish brown | 75 | deep yellowish brown |
|  | P | 89 | pale yellow | 86 | light yellow |
| Yeast extract-malt extract (ISP-2) | S | 23 | dark reddish gray | 23 | dark reddish gray |
|  | R | 58 | moderate brown | 71 | moderate olive |
|  | P | 71 | moderate olive | 71 | moderate olive |
| Oatmeal (ISP-3) | S | 22 | reddish gray | 23 | dark reddish gray |
|  | R | 86 | light yellow | 91 | dark grayish yellow |
|  | P | 89 | pale yellow | 87 | moderate yellow |
| Inorganic salts starch (ISP-4) | S | 23 | dark reddish gray | 23 | dark reddish gray |
|  | R | 87 | moderate yellow | 75 | deep yellowish brown |
|  | P | — | — | 87 | moderate yellow |
| Glycerol-asparagine (ISP-5) | S | 93 | yellowish gray | 63 | light brownish gray |
|  | R | 71 | moderate orange yellow | 71 | moderate orange yellow |
|  | P | 89 | pale yellow | 87 | moderate yellow |

*Determined by comparison with NBS Color Chips (SP 440. Color: Universal Language and Dictionary of Names. U.S. Government Printing Office, Washington, D.C. 20402) (SRM 2106. ISCC-NBS Centroid Color Charts. Office of Standard Reference Material, Room B311, Chem. Building, National Bureau of Standards, Washington, D.C. 20234).
S + Surface
R = Reverse
P = Pigment
Color determinations made on plates incubated 14 days at 28° C.

TABLE 3

Growth of *S. woolensis* and *S. amagasakensis* on Carbon Compounds in the Synthetic Medium of Shirling and Gottlieb*

| Synthetic Medium (ISP-9) | S. woolensis NRRL 12113 | S. amagasakensis ATCC 21325 |
|---|---|---|
| Negative Control (No carbon compound) | − | + |
| Positive Control D-glucose) | + | + |
| L-arabinose | + | ++ |
| Sucrose | ++ | ++ |
| D-xylose | ++ | ++ |
| Inositol | ++ | ++ |
| D-mannitol | ++ | ++ |
| D-fructose | ++ | ++ |
| Rhamnose | ++ | ++ |
| Raffinose | − | ± |
| Cellulose | − | ± |

++ = Strong utilization
+ = Positive utilization
± = Doubtful utilization
− = Negative utilization
* Shirling, E. B., and D. Gottlieb. 1966. Methods for characterization of Streptomyces species. Int. J. Syst. Bacteriol. 16:313-340.

TABLE 4

Cultural and Biochemical Characteristics* of *S. woolensis* and *S. amagasakensis*

| Medium | Determination | S. woolensis NRRL 12113 | S. amagasakensis ATCC 21325 |
|---|---|---|---|
| *Agar* | | | |
| Peptone-iron | S | Trace lavender-gray | Fair pale cream-white |
| | R | Pale yellow | Pale yellow-tan |
| | P | — | |
| | O | Melanin negative | Melanin negative |
| Calcium | S | Pale gray-tan | Gray-tan |
| malate | R | Cream-white | Pale cream-yellow |
| | P | — | — |
| | O | Malate partially solubilized | Malate partially solubilized |
| Glucose | S | Lavender-gray with cream-white sectors | Lavender-gray center; cream-white edge |
| asparagine | R | Yellow-tan | Yellow-tan |
| | P | Pale yellow | Pale yellow |
| Skim milk | S | Cream-white | Cream-white |
| | R | Yellow-tan | Orange-tan |
| | P | Yellow | Orange |
| | O | Casein solubilized | |
| Tyrosine | S | Lavender-gray-cream | Cream center; lavender-gray edge |
| | R | Orange-tan | Tan |
| | P | Orange-tan | Tan |
| | O | Tyrosine solubilized | Tyrosine solubilized |
| Xanthine | S | Lavender-gray | Lavender-gray center; white edge |
| | R | Very pale yellow | Very pale yellow |
| | P | Very pale yellow | Very pale yellow |
| | O | Xanthine not solubilized | Xanthine not solubilized |
| Nutrient | S | Lavender-gray | Mottled lavender-gray cream |
| Starch | R | Pale yellow | Yellow |
| | P | — | |
| | O | Starch slightly solubilized | Starch solubilized |
| Yeast extract | S | Lavender-gray cream | Lavender-gray cream |
| malt extract | R | Yellow-tan | Yellow-tan |
| | P | Pale yellow | Yellow |
| Peptone- | S | Pale yellow vegetative | Trace, very pale gray-white |
| yeast extract iron | R | Pale yellow | Yellow |
| (ISP-6) | P | Pale yellow | Yellow |
| | O | Melanin negative | Melanin negative |
| Tyrosine | S | Lavender-gray | Pale lavender-gray |
| (ISP-7) | R | Pale yellow | Pale yellow |
| | P | Pale yellow | Very pale yellow |
| | O | Melanin negative | Melanin negative |
| *Gelatin* | | | |
| Plain | S | Colorless or light tan surface ring | Tan surface pellicle |
| | P | — | — |
| | O | Liquefaction - ¼ Growth at bottom of tube - colorless | Liquefaction - ½ (1 tube); complete (1 tube) |
| Nutrient | S | Tan surface ring | Tan surface pellicle |
| | P | — | |
| | O | Trace liquefaction | Liquefaction - ½ (1 tube); complete (1 tube) |
| *Broth* | | | |
| Synthetic | S | — | White aerial on surface pellicle |
| nitrate | P | — | Pale yellow |
| | O | Flocculent, colorless bottom growth Nitrate reduced to nitrite | Flocculent, colorless bottom growth Nitrate reduced to nitrite |
| Nutrient nitrate | S | Yellow ring | Lavender-gray pink aerial growth on |

TABLE 4-continued

| | | Cultural and Biochemical Characteristics* of S. woolensis and S. amagasakensis | |
|---|---|---|---|
| Medium | Determination | S. woolensis NRRL 12113 | S. amagasakensis ATCC 21325 |
| | P | — | surface pellicle — |
| | O | Flocculent yellow bottom growth Nitrate reduced to nitrite | Flocculent yellow bottom growth Nitrate reduced to nitrite |
| Litmus milk | S | Blue-gray-tan ring Gray-pink aerial growth on surface pellicle | Blue-gray-tan ring Trace gray aerial growth on surface pellicle |
| | P | Red to lavender | Red-tan |
| | O | Peptonization Litmus reduced in one of two tubes pH 7.5 | Peptonization Litmus reduced in one of two tubes pH 7.2 |

The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, acetone, butanol, ethyl acetate and the like; and silica gel chromatography can be used to purify crude preparations of the antibiotic.

In a preferred recovery process, the compound produced by the subject process is recovered from the culture medium by separation of the mycelia and undissolved solids by conventional means, such as by filtration or centrifugation and solvent extraction of the filtered broth. The filtrate can be extracted with a solvent for antibiotic U-60,394, for example, methylene chloride, and the extract evaporated under reduced pressure to an aqueous concentrate. This preparation can be purified by chromatography on silica gel. The solvent system used for the chromatography is ethyl acetate:acetone:water (8:5:1) (v/v). Antibiotic U-60,394 is shown at $R_f$ 0.4 using standard bioautography on *Streptococcus pyogenes* UC 6055.

The antibiotic of the subject invention also can be recovered from fermentation broth by resin sorption on a resin comprising a non-ionic macro porous copolymer of styrene cross linked with divinylbenzene. Suitable resins are Amberlite XAD-2 and XAD-7, according to the procedure disclosed in U.S. Pat. No. 3,515,717. (Amberlite resins are available from Rohm and Haas, Philadelphia, Pa.). The antibiotic can be eluted from said resins by using acetone.

Salts of antibiotic U-60,394 also can be formed with inorganic or organic bases. Such salts can be prepared, as for example, by suspending antibiotic U-60,394 in water, adding a dilute base until the pH of the suspension is about 10.0 to 11.0, and freeze-drying to provide a dried residue consisting of the U-60,394 salt. Antibiotic U-60,394 salts with inorganic cations which can be formed include the sodium, potassium, and calcium salts. Other salts of U-60,394, including those with inorganic bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example the purine bases such as theophyllin, thiobromin, caffeine, or derivatives of such purine bases; antihistaminic bases which are capable of forming salts with weak acids, pyridine compounds such as nicotinic acid amide, isonicotinic acid hydrazide, and the like; phenylalkylamines such as adrenaline, ephedrine, and the like; choline, and others. Salts of U-60,394 can be used for the same biological purposes as the parent compound.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces woolensis* Dietz and Li sp.n., NRRL 12113, is used to inoculate 500 -ml. Erlenmeyer seed flasks containing 100 ml. of sterile medium consisting of the following ingredients:

|  | g./liter |
|---|---|
| Glucose monohydrate | 10 |
| Difco peptone | 10 |
| Difco yeast extract | 2.5 |
| Deionized water q.s. | 1 liter |

Difco products can be obtained from Difco Laboratories, Detroit, Mi.

The seed medium post-sterilization pH is ∼ 6.5. The seed inoculum is grown for three days at 28° C. on a Gump rotary shaker operating at 250 rpm and having a 2½inch stroke.

Seed inoculum (100 ml.), prepared as described above, is used to inoculate 500-ml. fermentation flasks (Erlenmeyer) containing 100 ml. of sterile fermentation medium consisting of the following ingredients:

|  | g./liter |
|---|---|
| Cerelose | 10 |
| Buffalo starch* | 10 |
| Phytone (BBL)** | 10 |
| $CaCO_3$ | 5 |
| NaCl | 2 |
| Tap water | Balance |

*now called National Starch. Fisher Scientific
**BBL, Div. of Becton, Dickinson & Co., Cockeysville, Md. 21030 U.S.A.

The inoculated fermentation medium is incubated at a temperature of 28° C. for 6 days on a Gump rotary shaker operating at 250 rpm and having a 2½inch stroke.

A typical six-day fermentation has the following titers of antibiotic in the fermentation broth:

| Day | Assay, BU/ml |
|---|---|
| 2 | 2.3 |
| 3 | 3.2 |
| 4 | 4.0 |
| 5 | 4.5 |
| 6 | 4.4 |

The assay is a *Sarcina lutea* disc plate assay using 0.1 M Tris buffer, pH 7.0 as diluent.

B. Recovery

To whole beer (ca. 10 l.) from a fermentation, as described above, is added 1 liter of diatomaceous earth (dicalite) at harvest pH 8.2. This slurry is filtered over a bed of Dicalite 4200 with suction. The filtrate is adjusted to about pH 4 with sulfuric acid and extracted 3 times with ⅓ volume methylene chloride. The combined organic phases are concentrated to 50 ml. on a rotary evaporator. Thin layer chromatography of this solution using silica gel with 8:5:1 (v/v) ethyl acetate:acetone:water shows antibiotic U-60,394 at $R_f$ 0.4 using bioautography on *S. pyogenes* UC 6055.

About 540 mg. of a prep of U-60,394, obtained as described above, is dissolved in 5 ml. of 5:3 (v/v) chloroform:methanol. The solution is loaded onto a 2.5×100 cm silica gel column. The column is eluted with three bed volumes of 8:5 (v/v) ethyl acetate:acetone and the activity is eluted by switching to 8:5:0.5 (v/v) ethyl acetate:acetone:$H_2O$. The active fractions are located by dipping 12.7 mm pads, removing the solvent and incubating on *S. pyogenes*-seeded agar trays. U-60,394 has an $R_f$ of +0.4 in 8:5:1 v/v ethyl acetate:acetone:water and reacted with ferric chloride spray (1:1 methanol: 5% $FeCT_3$) to give a yellow-orange color. The eluates are pooled and then concentrated on a rotary evaporator to give a solid preparation of essentially pure U-60,394. This material is dissolved in hot methanol and filtered. Water is added to cloudiness, and the solution is allowed to cool to room temperature. Yellowish-green crystalline needles of antibiotic U-60,394 form and are collected by standard procedures.

We Claim:

1. Antibiotic U-60,394, which is active against Gram-positive bacteria, and which in its essentially pure crystalline form has the following characteristics:
   (a) molecular weight of 391.08014 (high resolution mass spectrometry);
   (b) color and form of crystals: yellowish-green needles;
   (c) is insoluble in water, soluble in methanol and acetone with difficulty, and easily soluble in ethyl acetate, methylene chloride and dimethylsulfoxide;
   (d) a characteristic $^{13}$C-NMR spectrum as shown in FIG. 1 of the drawings;
   (e) a characteristic $^{1}$H-NMR spectrum as shown in FIG. 2 of the drawings;
   (f) a characteristic UV spectrum as shown in FIG. 3 of the drawings;
   (g) a characteristic infrared absorption spectrum when dissolved in a mineral oil mull as shown in FIG. 4 of the drawings;
   (h) a melting point of 265° C. to 266° C. with decomposition; and
   base addition salts thereof.

2. A process for preparing antibiotic U-60,394 which comprises cultivating *Streptomyces woolensis* Dietz and Li sp.n., having the identifying characteristics of NRRL 12113, in an aqueous nutrient medium under aerobic conditions until substantial antibiotic U-60,394 activity is imparted to said medium.

3. A process, according to claim 2, wherein said aqueous nutrient medium contains a source of assimilable carbohydrate and assimilable nitrogen.

4. A process for recovering antibiotic U-60,394 from a fermentation beer which comprises:
   (a) filtering said beer to obtain filtered beer containing antibiotic U-60,394;
   (b) adjusting the pH of the filtrate to about 4.0;
   (c) extracting said filtrate with a solvent for U-60,394 to obtain an extract containing antibiotic U-60,394;
   (d) evaporating said extract to an aqueous concentrate; and
   (e) purifying said extract by chromatographic means to obtain essentially pure antibiotic U-60,394.

5. A process, according to claim 4, wherein said filtered beer is extracted with methylene chloride.

6. A process, according to claim 4, wherein said aqueous concentrate is subjected to chromatography on silica gel using the solvent system ethyl acetate:acetone 8:5 and then ethyl acetate:acetone:water (8:5:0.5) to obtain essentially pure preparations of antibiotic U-60,394.

7. A process for recovering antibiotic U-60,394 from a fermentation beer which comprises:

(a) filtering said fermentation beer to obtain filtered beer;

(b) extracting said filtered beer with methylene chloride to obtain an extract containing antibiotic U-60,394;

(c) evaporating said extract under reduced pressure to an aqueous concentrate; and (d) chromatographing said extract on silica gel using the solvent systems ethyl acetate:acetone (8:5) and then ethyl acetate:acetone:water (8:5:0.5) to obtain essentially pure antibiotic U-60,394.

8. A biologically pure culture of the microorganism *Streptomyces woolensis* Dietz and Li sp.n., having the identifying characteristics of NRRL 12113, said culture being capable of producing the antibiotic U-60,394 in a recoverable quantity upon fermentation in an aqueous nutrient medium containing assimilable sources of carbon, nitrogen and inorganic substances.

* * * * *